US011020536B2

(12) United States Patent
Saussaye et al.

(10) Patent No.: US 11,020,536 B2
(45) Date of Patent: Jun. 1, 2021

(54) MANUAL INJECTION DEVICE

(71) Applicant: APTAR FRANCE SAS, Le Neubourg (FR)

(72) Inventors: Anthony Saussaye, Louviers (FR); Quentin Jaouen, Gournay en Bray (FR)

(73) Assignee: APTAR FRANCE SAS, Le Neubourg (FR)

( * ) Notice: Subject to any disclaimer, the term of this patent is extended or adjusted under 35 U.S.C. 154(b) by 148 days.

(21) Appl. No.: 16/334,893

(22) PCT Filed: Oct. 2, 2017

(86) PCT No.: PCT/FR2017/052691
§ 371 (c)(1),
(2) Date: Mar. 20, 2019

(87) PCT Pub. No.: WO2018/065708
PCT Pub. Date: Apr. 12, 2018

(65) Prior Publication Data
US 2019/0298934 A1 Oct. 3, 2019

(30) Foreign Application Priority Data
Oct. 4, 2016 (FR) ...................................... 1659543

(51) Int. Cl.
*A61M 5/32* (2006.01)
*A61M 5/315* (2006.01)

(52) U.S. Cl.
CPC ........ *A61M 5/326* (2013.01); *A61M 5/31515* (2013.01); *A61M 5/3272* (2013.01);
(Continued)

(58) Field of Classification Search
CPC ................ A61M 5/326; A61M 5/3272; A61M 5/31515; A61M 2205/581;
(Continued)

(56) References Cited

U.S. PATENT DOCUMENTS

2010/0160894 A1\* 6/2010 Julian ....................... A61P 1/04
604/506
2013/0317435 A1\* 11/2013 Fabien ................ A61M 5/3157
604/135
(Continued)

FOREIGN PATENT DOCUMENTS

FR 3 013 601 A1 5/2015
WO 2006/111862 A1 10/2006
(Continued)

OTHER PUBLICATIONS

International Preliminary Report on Patentability with English Translation of Written Opinion dated Apr. 9, 2019 for PCT/FR2017/052691.
(Continued)

*Primary Examiner* — Theodore J Stigell
*Assistant Examiner* — Daniel Moore
(74) *Attorney, Agent, or Firm* — Sughrue Mion, PLLC

(57) ABSTRACT

A manual injection device having a lower body (1) for a reservoir (S), a piston (P) and a needle (A); a movable upper body (2) including a piston rod (TP); and an actuator sleeve (10) including a contact end (11) and movable relative to the lower body between projecting positions and an actuated position. The actuator sleeve (10) is in a first projecting position before the manual injection device is actuated, and in a second projecting position after it is actuated. The actuator sleeve co-operates with the lower body (1) or with any element secured to the lower body to define a pricking lock. The piston rod (TP) co-operates with the reservoir or with an element secured to the reservoir to define an injection lock. The force for actuating the pricking lock is less than the force for actuating the injection lock, such that the pricking lock is actuated first.

16 Claims, 9 Drawing Sheets

(52) U.S. Cl.
CPC .............. *A61M 5/31505* (2013.01); *A61M 2005/31508* (2013.01); *A61M 2005/3247* (2013.01); *A61M 2005/3267* (2013.01); *A61M 2205/581* (2013.01)

(58) Field of Classification Search
CPC .... A61M 5/31505; A61M 2005/31508; A61M 2005/3247; A61M 2005/3267; A61M 5/31578; A61M 5/3158; A61M 5/3243; A61M 5/3257; A61M 5/3202; A61M 2005/3284

See application file for complete search history.

(56) References Cited

U.S. PATENT DOCUMENTS

| | | | | |
|---|---|---|---|---|
| 2014/0303564 | A1* | 10/2014 | Roberts | A61M 5/3271 604/198 |
| 2015/0174335 | A1* | 6/2015 | Roervig | A61M 5/31553 604/198 |

FOREIGN PATENT DOCUMENTS

| | | | |
|---|---|---|---|
| WO | 2006/129196 | A1 | 12/2006 |
| WO | 2011/047298 | A2 | 4/2011 |
| WO | 2014/150201 | A1 | 9/2014 |
| WO | 2015/075399 | A1 | 5/2015 |

OTHER PUBLICATIONS

International Search Report for PCT/FR2017/052691 dated Jan. 19, 2018 [PCT/ISA/210].

* cited by examiner

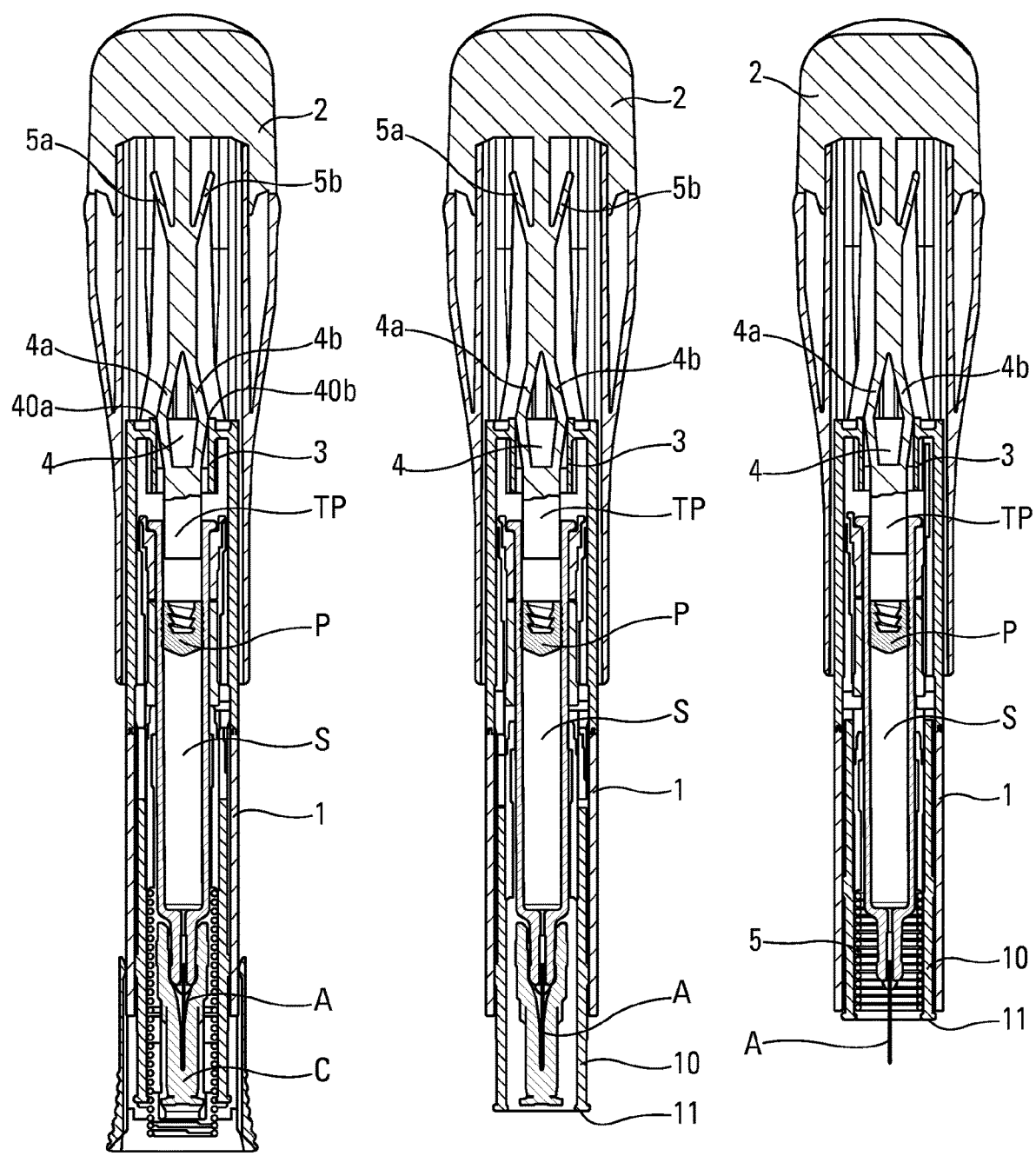

MANUAL INJECTION DEVICE

CROSS REFERENCE TO RELATED APPLICATIONS

This application is a National Stage of International Application No. PCT/FR2017/052691 filed Oct. 2, 2017, claiming priority based on France Patent Application No. 1659543 filed Oct. 4, 2016.

The present invention relates to a manual injection device.

The purpose of manual injection devices is mainly to cause the needle to penetrate into the patient's body, and also to protect the needle of the syringe before, during, and after injection. In contrast, the actual injection of the fluid contained in the syringe into the patient's body is done manually by the user. Manual injection devices are relatively complex devices that must satisfy a certain number of constraint requirements in order to be reliable. The robustness of the device, its handling, and its ease of use for the user are also important elements. In addition, since most manual injection devices are for single use, the cost of manufacture and of assembly is also a factor that needs to be taken into account.

Numerous manual injection devices exist on the market, but they all present a certain number of drawbacks.

Thus, use of the manual injection device must not be too difficult, as this would prevent weak people from using it. It is also necessary to avoid injection beginning before the needle has penetrated into the patient's body. Furthermore, in order to avoid any risk of injury before and after using the device, the manual injection device should include a needle safety device that avoids the needle being visible before and after the device is used. Obviously, the safety device should also be reliable and not be released too easily. It should also be functional even when the user actuates the manual injection device poorly, e.g. when the user removes it too soon from the body, before the end of injection.

Documents WO 2015/075399, WO 2014/150201, WO 2011/047298, WO 2006/129196, and WO 2006/111862 describe prior-art devices.

An object of the present invention is to provide a manual injection device that does not have the above-mentioned drawbacks, and that makes it possible to satisfy the various major requirements and constraints for safe and reliable use of the manual injection device.

In particular, an object of the present invention is to provide a manual injection device that avoids the risk of fluid injection beginning before the needle has penetrated fully into the injection site.

Another object of the present invention is to provide a manual injection device that is reliable in use, that is safe and that prevents any risk of injury, and that is simple and inexpensive to manufacture, to assemble, and to use.

The present invention thus provides a manual injection device comprising:

- a lower body that receives a reservoir, said reservoir being stationary axially relative to said lower body and containing fluid to be injected, said reservoir including a piston and a needle;
- an upper body that is movable axially relative to said lower body during actuation, said upper body including a piston rod that co-operates with said piston during injection so as to move it in the reservoir; and
- an actuator sleeve that includes a contact end for coming into contact with the user's body, said actuator sleeve being movable relative to said lower body between projecting positions in which said actuator sleeve projects, at least in part, out from said lower body, and an actuated position in which said actuator sleeve is moved axially into said lower body, said actuator sleeve being in a first projecting position before the manual injection device has been actuated, and in a second projecting position after the manual injection device has been actuated;

said actuator sleeve co-operating with said lower body, or with any element that is secured to said lower body, such as a reservoir support, to define a pricking lock, and said piston rod co-operating with said reservoir, or with any element that is secured to said reservoir, such as a reservoir support or such as said lower body, to define an injection lock, the force necessary for actuating said pricking lock being less than the force necessary for actuating said injection lock, such that said pricking lock is actuated before said injection lock.

Advantageously, one of said actuator sleeve and said lower body, or any element that is secured to said lower body, includes a flexible tab that is adapted to deform laterally relative to said actuator sleeve and/or relative to said lower body when said actuator sleeve is moved from its first projecting position to its actuated position, and then from its actuated position while returning to its second projecting position, the other of said actuator sleeve and said body, or any element that is secured to said lower body, including an initial zone that co-operates with said flexible tab in said first projecting position, an intermediate zone that co-operates with said flexible tab in said actuated position, and a final reception zone that co-operates with said flexible tab in said second projecting position, said final reception zone being offset, at least laterally, from said initial zone.

Advantageously, a deformable axial wall is adapted to deform resiliently so as to allow said flexible tab to pass from said initial zone to said intermediate zone, said deformable axial wall, in its non-deformed position, then being adapted to guide said flexible tab from said intermediate zone to said final reception zone.

Advantageously, said final reception zone is connected to said intermediate zone via a final groove, an axial shoulder being provided between said final reception zone and said final groove, said flexible tab being adapted to slide in said final groove when said actuator sleeve returns from its actuated position to its second projecting position, said flexible tab becoming snap-fastened below said axial shoulder when said actuator sleeve reaches its second projecting position after use, thereby locking said actuator sleeve relative to said body.

In a first advantageous embodiment, said piston rod includes a central recess that defines two flexible branches that slope radially away from each other so as to form a radially-outer shoulder on each side of said piston rod.

Advantageously, said radially-outer shoulders co-operate with an axial flange that is secured to an element that is fastened to said lower body.

Advantageously, said radially-outer shoulders co-operate with a radial collar of said reservoir.

Advantageously, each radially-outer shoulder defines an indented profile, said indented profiles receiving a radial projection of an axial flange that is secured to an element that is fastened to said lower body.

In a second advantageous embodiment, before actuation, said piston rod is connected via breakable bridges to an element that is stationary relative to said reservoir.

Advantageously, before actuation, said piston rod is connected to a disk that is fastened to said lower body.

In a variant, before actuation, said piston rod is connected to a ring that is fastened, in particular crimped, on a radial collar of said reservoir.

In an advantageous embodiment, before actuation, said piston rod is connected to a ring that is fastened, in particular crimped, on a radial collar of said reservoir, said ring including a radially-inner projection that, before actuation, co-operates with a groove of said piston rod.

These and other characteristics and advantages of the present invention appear more clearly from the following detailed description, given by way of non-limiting examples, and with reference to the accompanying drawings, and in which:

FIG. 1 is a diagrammatic section view of a manual injection device in a first advantageous embodiment, before use;

FIG. 2 is a view similar to the view in FIG. 1, after the protective cap has been removed from the needle, in its rest position, before pricking;

FIG. 3 is a view similar to the view in FIG. 2, at the end of pricking, before the injection lock has been triggered;

Figure 4:
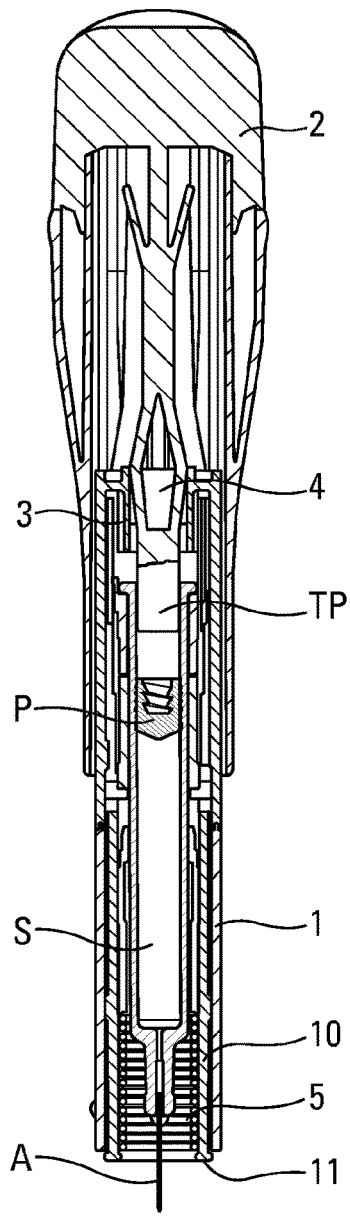
FIG. 4 is a view similar to the view in FIG. 3, after the injection lock has been triggered.
Figure 5:
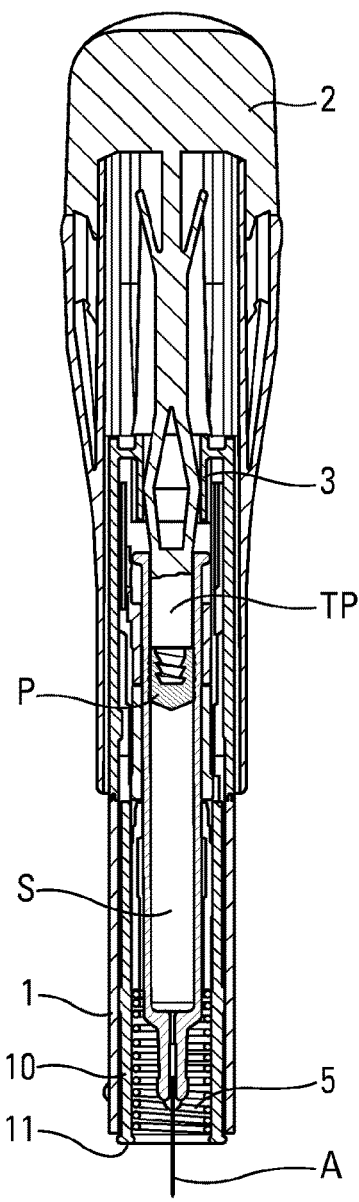
FIG. 5 is a view similar to the view in FIG. 4, at the beginning of injection.
Figure 6:
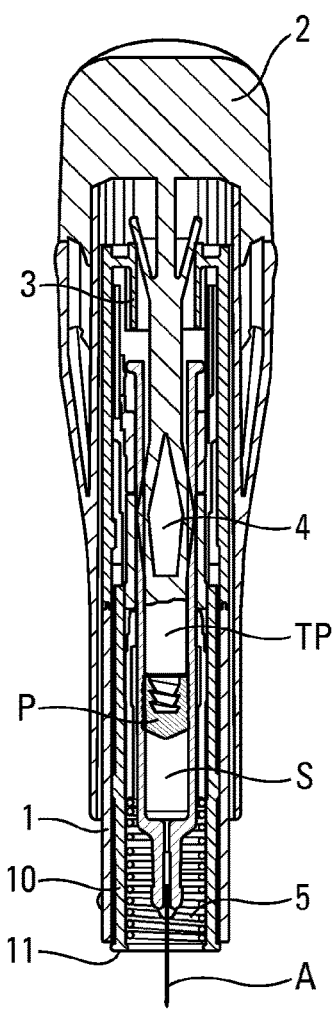
FIG. 6 is a view similar to the view in FIG. 5, during injection.
Figure 7:
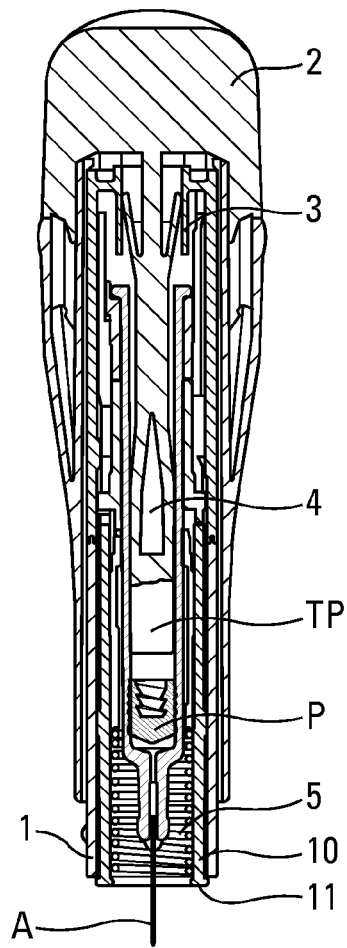
FIG. 7 is a view similar to the view in FIG. 6, at the end of injection, before the post-injection safety device has been triggered.
Figure 8:
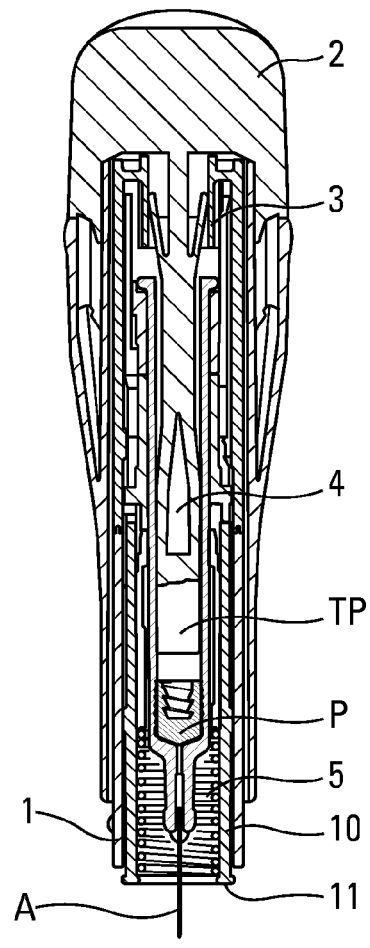
FIG. 8 is a view similar to the view in FIG. 7, at the end of injection, after the post-injection safety device has been triggered.

The manual injection device shown in the figures comprises a lower body 1 and an upper body 2 that is movable axially relative to said lower body 1 during actuation. It should be observed that the lower body 1 and the upper body 2 may each be made as a single piece or else out of a plurality of assembled-together portions. In said lower body 1, an actuator sleeve 10 slides axially, the actuator sleeve 10 having a bottom end 11 ("bottom" in the orientation in FIG. 1) that is for coming into contact with the patient's body around the injection zone. In known manner, the lower body 1 contains a reservoir S containing the fluid to be injected, a needle A that is fastened to said reservoir S and through which the fluid is dispensed, and a piston P that is adapted to move in said reservoir S so as to perform the injection. The upper body 2 includes a piston rod TP that co-operates with said piston P during injection so as to move it in the reservoir S. Before use, the needle A may be protected by a protective cap C, shown in FIG. 1. Typically, the reservoir S may be a conventional pre-filled syringe, provided with a radial collar 9. Said reservoir S is stationary relative to said lower body 1, and said piston rod TP is stationary relative to said upper body 2. Thus, when the upper body 2 slides axially relative to the lower body 1, the piston rod TP slides axially relative to the reservoir S.

Before actuation, the actuator sleeve 10 is in a first projecting position in which it surrounds the needle A, thereby forming a pre-injection safety device. During actuation, the actuator sleeve 10 slides inside the lower body 1 towards an actuated position, so as to expose the needle A and enable pricking, and injection of the fluid. After injection, the actuator sleeve 10 returns into a second projecting position in which it is once again arranged around the needle A, so as to avoid any risk of injury with said needle A, thereby forming a post-injection safety device. The actuator sleeve 10 is advantageously urged towards its projecting positions by a spring 5 that may be of any type.

The actuator sleeve 10 co-operates with the lower body 1 (or with any element that is secured to said lower body 1, such as the reservoir support, for example), so as to define a pricking lock, and the piston rod TP co-operates with said reservoir S (or with any element that is secured to said reservoir S, such as the reservoir support or the lower body, for example), so as to define an injection lock.

In the invention, the pricking lock is actuated before the injection lock, i.e. the axial force necessary for triggering the pricking lock is less than the axial force necessary for triggering the injection lock. Thus, when the user presses the device against the injection site and presses axially on the upper body 2 so as to cause it to slide axially relative to the lower body 1, the actuator sleeve 10 initially moves axially inside the lower body 1 so as to perform pricking. The piston rod TP moves axially inside the lower body 1 only after said actuator sleeve 10 has reached its actuated position.

FIGS. 1 to 18 show a first advantageous embodiment. FIGS. 1 to 9 show various positions in the actuation sequence of the manual injection device, and FIGS. 10 to 18 show variant embodiments of the injection lock and the blocking system for blocking the piston after injection.

Figure 9:
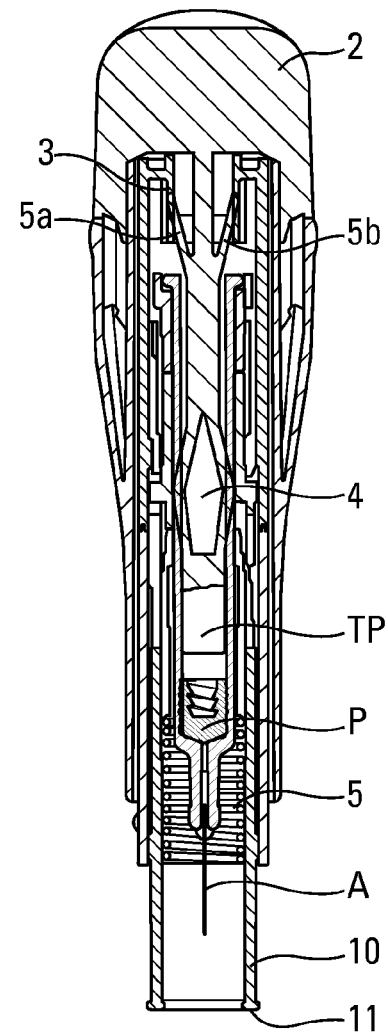
FIG. 9 is a view similar to the view in FIG. 8, at the end of use, after the post-injection safety device has been actuated.

With reference to FIGS. 1 to 9, it should be observed that after removing the protective cap C, the user presses the bottom end 11 of the actuator sleeve 10 around the injection site, and exerts axial pressure on the upper body 2. Since the resistance to the injection lock triggering, as described below, is greater than the resistance of the pricking lock, as also described below, it is the actuator sleeve 10 that initially slides axially into the lower body 1. This uncovers the needle A, which thus penetrates into the injection site under the effect of said axial pressure from the user. It is only when the actuator sleeve 10 reaches its actuated position, shown in FIGS. 3 and 4, that the actuation force or axial pressure of the user serves to trigger the injection lock. After triggering said injection lock, the upper body 2, and thus also the piston rod TP, move axially relative to the lower body 1 and thus relative to the reservoir S, so as to move the piston P in the reservoir S and thus inject the fluid contained in the reservoir through the needle A and into the injection site. At the end of injection, when the user removes the manual injection device from the injection site, the actuator sleeve 10 returns automatically, e.g. under the effect of the return spring 5, to its second projecting position in which it is locked, so as to avoid any risk of injury with the needle A, as can be seen in FIG. 9.

Figure 10:
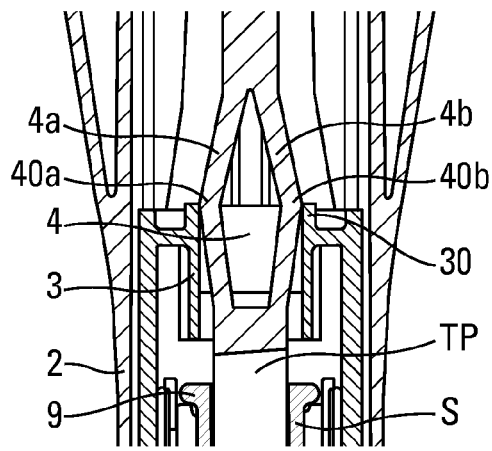
FIGS. 10 and 11 are views of a detail of a first variant embodiment of the injection lock.
Figure 11:
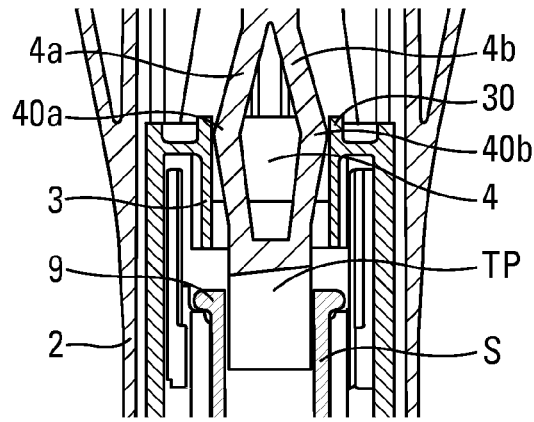

FIGS. 10 and 11 show a first variant embodiment of the injection lock. In this variant, the piston rod TP includes a central recess 4 that defines two flexible branches 4a, 4b that slope radially away from each other so as to form a radially-outer shoulder 40a, 40b on each side of the piston rod TP. The shoulders 40a, 40b co-operate with an axial flange 30 that is secured to an element 3 that is fastened to said lower body 1. In order to trigger the injection lock, it is necessary to deform said branches 4a, 4b radially inwards, so as to enable said shoulders 40a, 40b to pass axially beyond said flange 30. The axial force necessary to do this is greater than the axial force necessary for triggering the pricking lock, which guarantees that injection begins only after the end of pricking.

Figure 12:
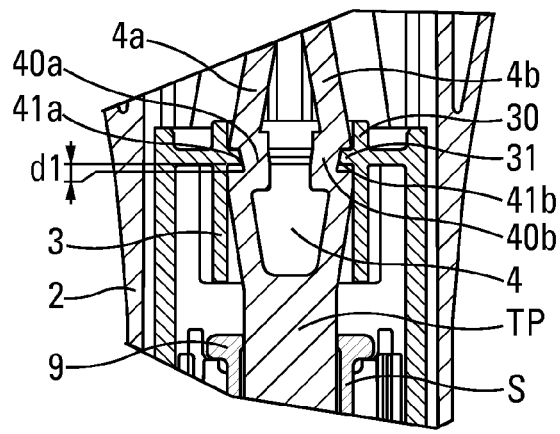
FIGS. 12 to 14 are views of a detail of a second variant embodiment of the injection lock.
Figure 13:
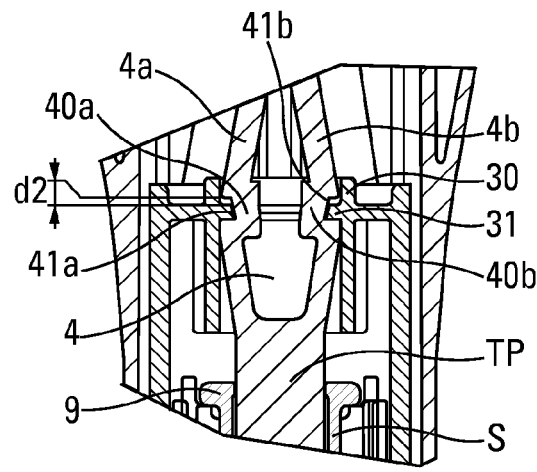
Figure 14:
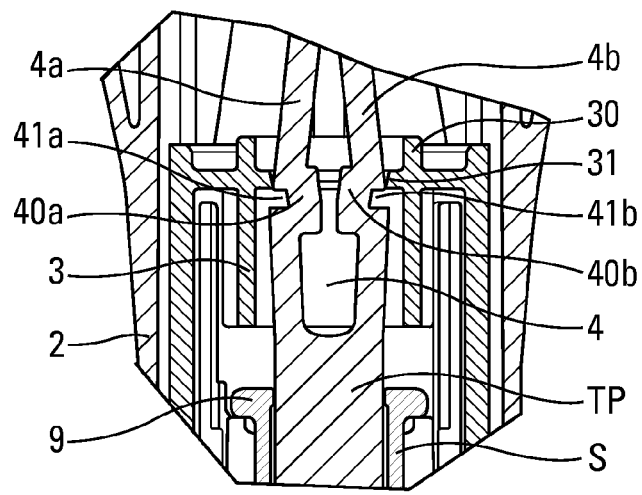
Figure 15:
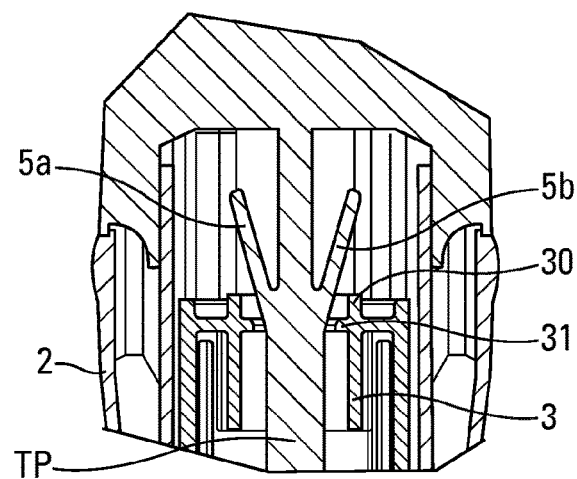
FIGS. 15 to 18 are views of a detail of a variant embodiment of the blocking system for blocking the piston after injection.
Figure 16:
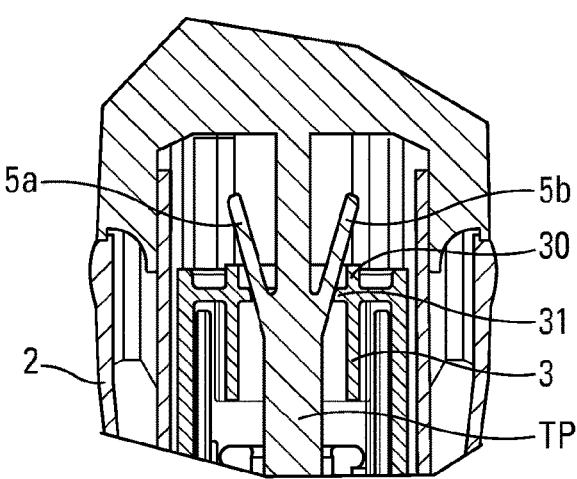
Figure 17:
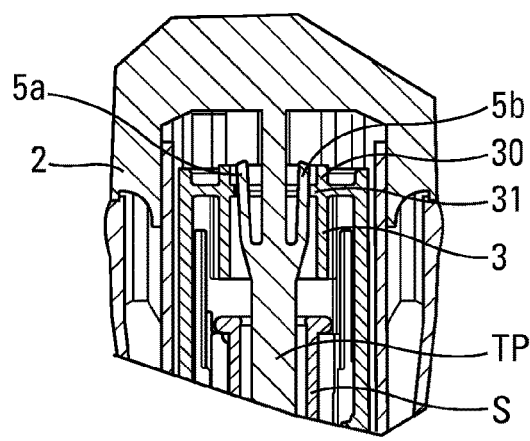

FIGS. 12 to 14 show another variant embodiment of the pricking lock. In this variant, each of the two radially-outer shoulders 40a, 40b defines an indented profile 41a, 41b, the indented profiles receiving a radial projection 31 of said axial flange 30. In this variant, a tear-off protection function is also provided, by snap-fastening the profiles 41a, 41b on the projection 31, preventing the piston rod TP from being pulled out of the reservoir S. Preferably, clearance is provided for such snap-fastening, represented in FIGS. 12 and 13 by the distances d1 and d2.

Figure 18:
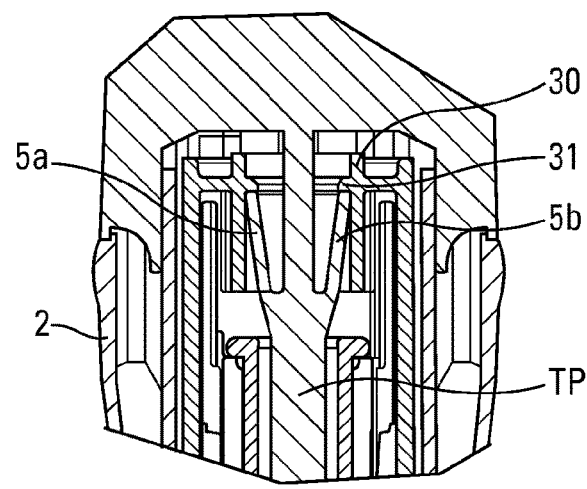
Figure 19:
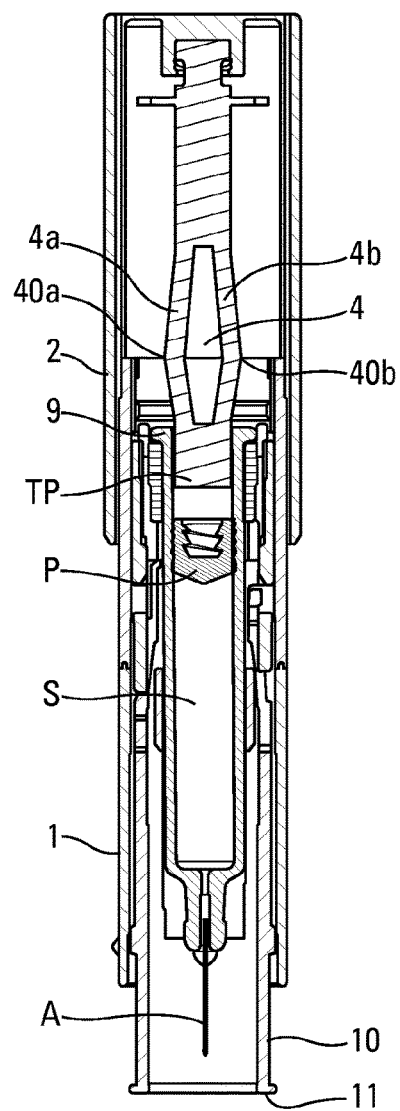
FIG. 19 is a diagrammatic section view of a manual injection device in a second advantageous embodiment, before use.
Figure 20:
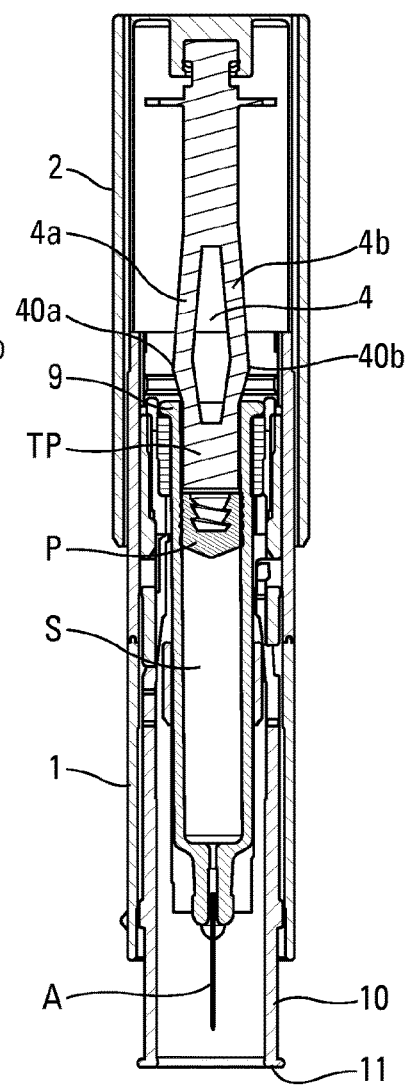
FIG. 20 is a view similar to the view in FIG. 19, at the beginning of pricking.
Figure 21:
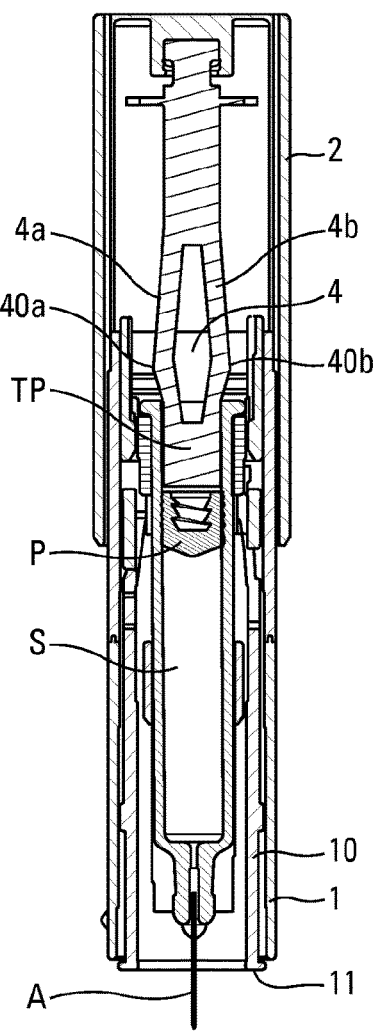
FIG. 21 is a view similar to the view in FIG. 20, at the end of pricking, before the injection lock is triggered.
Figure 22:
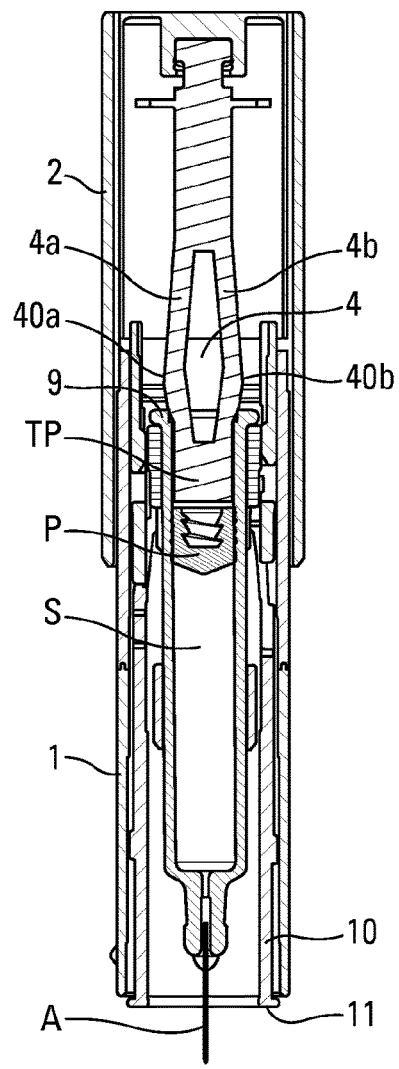
FIG. 22 is a view similar to the view in FIG. 21, at the beginning of injection.
Figure 23:
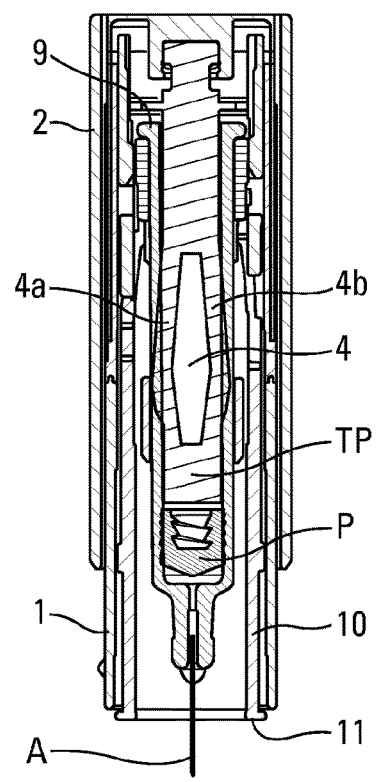
FIG. 23 is a view similar to the view in FIG. 22, at the end of injection.
Figure 24:
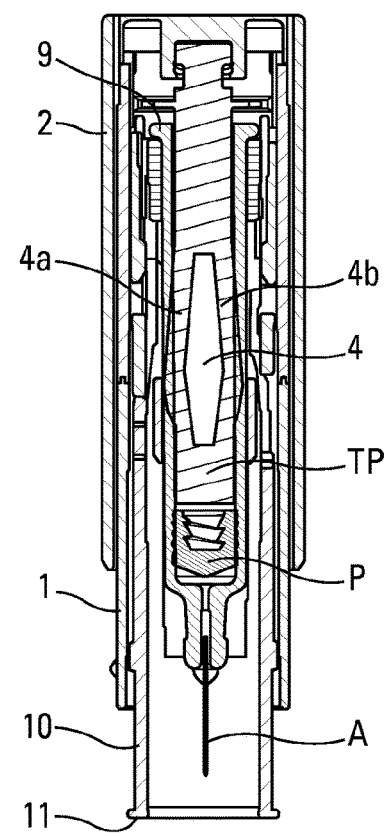
FIG. 24 is a view similar to the view in FIG. 23, at the end of use, after the post-injection safety device has been actuated.
Figure 25:
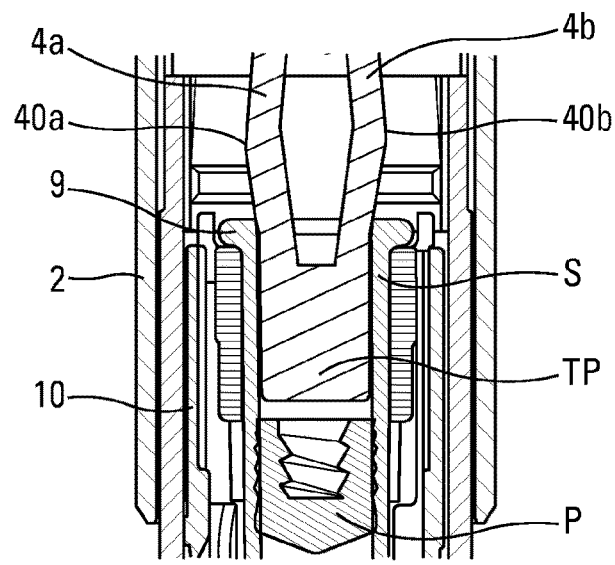
FIGS. 25 to 29 are views of a detail of several variant embodiments of the injection lock.

FIGS. 15 to 18 show a variant embodiment of a blocking device for blocking the piston after use. In this variant, the piston rod TP includes, in its portion at the rear (relative to the piston P), two flexible tabs 5a, 5b that extend axially towards the rear, flaring radially outwards. At the end of injection, the flexible tabs 5a, 5b deform radially inwards on passing through the projection 31 of the flange 30, so as to become snap-fastened beneath it, as can be seen in FIG. 18. This blocks the piston rod TP in the lower body 1 and thus blocks the piston P in the reservoir S. Naturally, this device could be adapted to a pricking lock as shown in FIGS. 10 and 11, which could thus include a projection 31 on its axial flange 30.

FIGS. 19 to 29 show a second advantageous embodiment. FIGS. 19 to 24 show various positions in the actuation sequence of the manual injection device, and FIGS. 25 to 29 show variant embodiments of the injection lock. The actuation sequence is similar to the actuation sequence of the first embodiment, beginning with pricking, followed by injection.

The structure of the manual injection device is simplified, with the piston rod TP snap-fastened at its rear end (remote from the piston P) in the upper body 2.

The main difference relates to the injection lock, formed in FIGS. 19 to 25 between the piston rod TP and the radial collar 9 of the syringe S. In this variant embodiment, the piston rod TP is made as in the first embodiment with a central recess 4 that defines two branches 4a, 4b that slope radially away from each other so as to form a shoulder 40a, 40b on each side. The shoulders 40a, 40b co-operate with said radial collar 9 of the syringe S.

Figure 26:
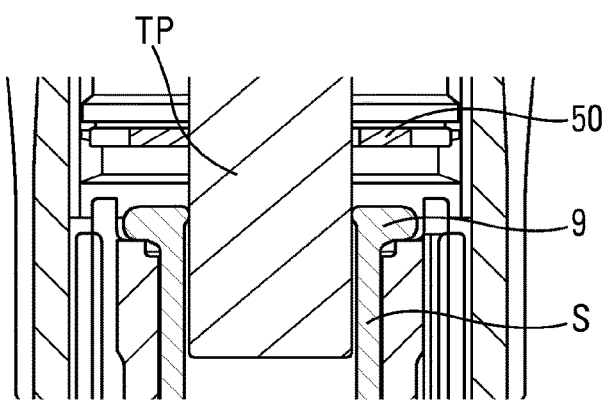
Figure 27:
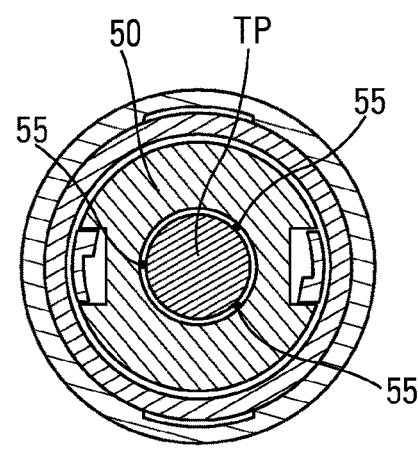

FIGS. 26 and 27 show another advantageous variant in which a disk 50, that is stationary relative to the lower body 1 and thus relative to the reservoir S, is connected, before actuation, to the piston rod TP via breakable bridges 55, typically three breakable bridges, as can be seen in FIG. 27. The resistance of the breakable bridges 55 against breaking is greater than the force for triggering the pricking lock, such that pricking takes place before injection.

Figure 28:
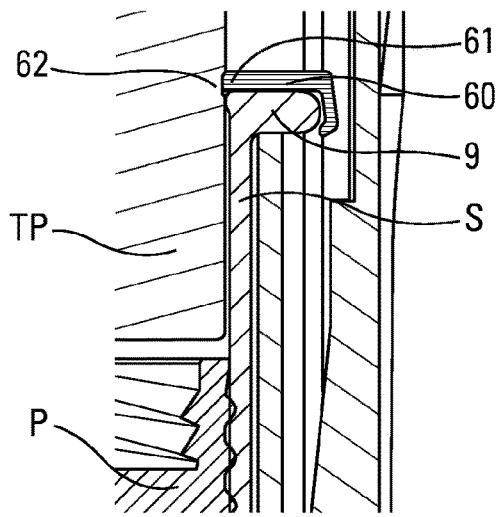

FIG. 28 shows another variant in which a crimping ring 60 is fastened directly on the radial collar 9 of the syringe, said ring 60 including a radially-inner projection 61 that, prior to actuation, co-operates with a groove 62 of the piston rod TP. The force necessary for disengaging said projection 61 from said groove 62 is greater than the force for triggering the pricking lock, such that pricking takes place before injection.

Figure 29:
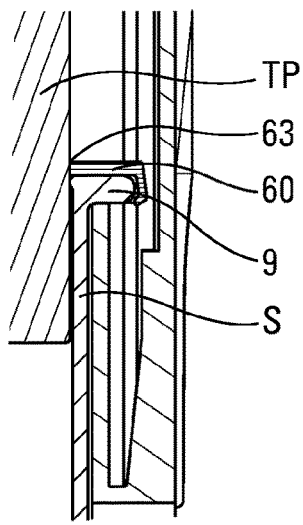

FIG. 29 shows yet another variant in which said radially-inner projection 61 of the crimping ring 60 is fastened to said piston rod TP via breakable bridges 63. The resistance of the breakable bridges 63 against breaking is greater than the force for triggering the pricking lock, such that pricking takes place before injection.

Other variants of the pricking lock may be envisaged.

FIGS. 30 to 38 show advantageous embodiments of the pricking lock and of the pre- and post-injection safety devices. These devices apply to both of the above-described embodiments and to the various variants.

Advantageously, one of said actuator sleeve 10 and said lower body 1 (or an element that is secured to said lower body 1) includes a flexible tab 110 that is adapted to deform laterally relative to said actuator sleeve 10 and/or relative to said lower body 1 receiving the reservoir S, when said actuator sleeve 10 is moved from its first projecting position to its actuated position, and then from its actuated position while returning to its second projecting position.

A first advantageous embodiment of a pricking lock is shown in FIGS. 30 to 35. In this embodiment, the actuator sleeve 10 includes an initial groove 101, advantageously a sloping groove, that extends from an initial zone 102 to an intermediate zone 105. Said initial groove 101 preferably includes an elastically-deformable axial wall 1020. Said actuator sleeve 10 also includes a final reception zone 106 that is offset, at least laterally, relative to said initial zone 102, and that is connected to said intermediate zone 105 via a final groove 107, advantageously a sloping groove. An axial shoulder 108 is provided between said final reception zone 106 and said final groove 107.

The lower body 1 includes a tab 110 that is laterally flexible, i.e. it deforms in the peripheral direction of the body. The flexible tab 110 advantageously includes a head 112 that co-operates with the grooves and shoulders of the actuator sleeve 10, as described below.

More particularly, FIGS. 30 to 35 show the operation of the pricking lock formed between the actuator sleeve 10 and the lower body 1.

Figure 30:
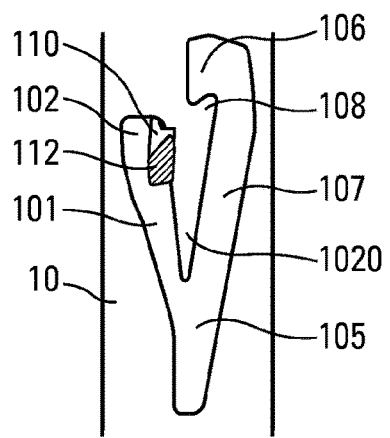
FIGS. 30 to 35 are diagrammatic and fragmentary views showing, in detail, the pricking lock during various sequences of use of the FIG. 1 manual injection device.
Figure 31:
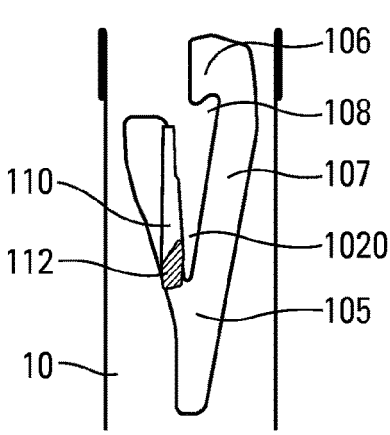

FIG. 30 shows the start position, i.e. when the user begins to use the manual injection device. In FIG. 30, it can be seen that the head 112 of the flexible tab 110 is arranged in said initial zone 102. When the actuator sleeve 10 slides into the lower body 1, said head 112 of the flexible tab 110 slides inside said initial groove 101. When the head 112 reaches the position in FIG. 31, in which it co-operates on one side with the initial groove 101 and on the other side with the deformable axial wall 1020, it deforms said deformable axial wall 1020 laterally, so as to be able to continue its actuation stroke. The deformation of the deformable axial wall 1020 enables the head 112 of the flexible tab 110 to pass into the intermediate zone 105. Optionally, when said deformable axial wall 1020 is fully deformed, it may generate a sound, such as a click, so as to signal to the user that injection is about to begin.

Figure 32:
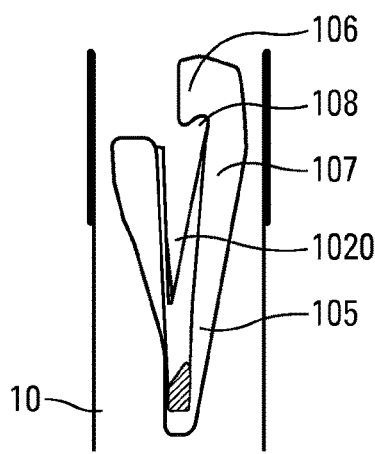

In the position shown in FIG. 32, the actuator sleeve 10 has reached its actuated position in which the needle A has penetrated into the injection zone of the patient as far as the injection position, and in which injection may begin. In this actuated position of the actuator sleeve 10, the head 112 of the flexible tab 110 is in the intermediate zone 105. In this position, the deformable axial wall 1020 has returned elastically to its non-deformed position, such that said intermediate zone 105 is connected to said final reception zone 106 via said sloping final groove 107.

Figure 33:
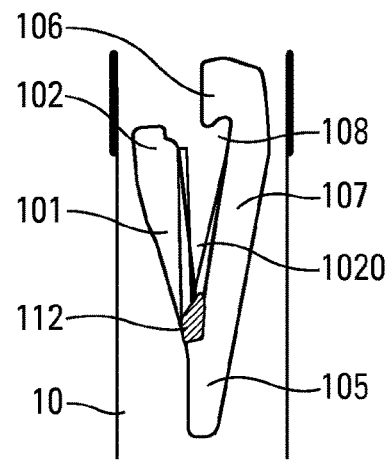

When said actuator sleeve 10 returns from its actuated position to its second projecting position under the effect of the spring 5, said head 112 of the flexible tab 110 slides into said sloping final groove 107. FIG. 33 is a diagram showing that the flexible tab 110, in particular the head 112, can no longer return into said initial groove 101 as a result of the deformable axial wall 1020 that prevents the passage of said head 112. Advantageously, said head 112 includes a front wall that slopes at least in part, and that co-operates with the sloping end of said deformable axial wall 1020, so as to guide said head into the sloping final groove 107. Thus, the deformable axial wall 1020 forms an integral part of the cam, formed by the final groove 107, that guides the flexible tab 110 towards the final reception zone 106.

Figure 34:
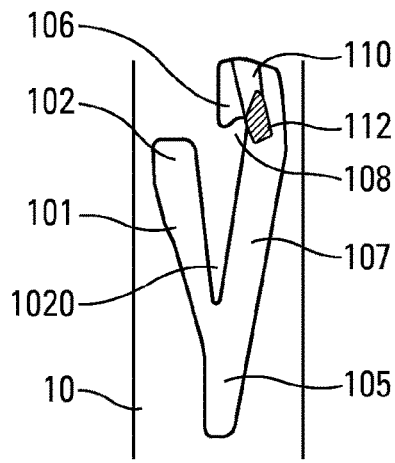
Figure 35:
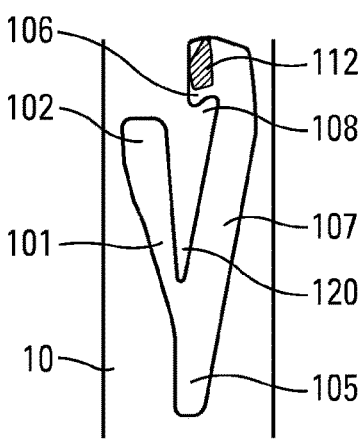

When said actuator sleeve 10 reaches its second projecting position after use, said head 112 becomes snap-fastened in said final reception zone 106 below said axial shoulder 108, thereby locking said actuator sleeve 10 relative to said lower body 1. From this locked position, said actuator sleeve 10 can no longer be moved towards its actuated position, as a result of the abutment formed between the head 112 of the flexible tab 110 and the axial shoulder 108. The lateral deformation of the flexible tab 110 during actuation, in particular in the sloping final groove 107 as shown in FIG. 34, causes the head 112 to snap-fasten resiliently and automatically below the axial shoulder 108 when the head 112 arrives in said final reception zone 106, as shown in FIG. 35. The post-injection safety device is thus in its locked final position. Thus, the needle A is completely protected after use, and the user can no longer use the manual injection device and/or be injured by the needle. Optionally, the snap-fastening in the final reception zone 106 may generate a sound, such as a click, so as to inform the user that the locked final position has been reached.

The above-described pricking lock of the actuator sleeve is particularly effective and reliable, while being robust and easy, and thus inexpensive, to mold and to assemble. In particular, it comprises only two parts, the actuator sleeve 10 and the lower body 1.

Naturally, the shapes of the grooves, their dimensions, and their slopes may be modified as a function of the needs of and the characteristics desired for the needle safety device. In particular, the initial groove may be axial or sloping. It may lead directly to the intermediate zone, without there being second and third grooves. With a sloping initial groove, the final groove could be axial or also sloping. Furthermore, the pricking lock does not necessarily include the above-described deformable axial wall 1020.

Other variants may also be envisaged.

In particular, the flexible tab 110 could be formed on an element that is secured to said lower body 1 and not directly in said lower body 1. In particular, the flexible tab 110 could be formed on the support of the reservoir S, that holds said reservoir in stationary manner in said lower body 1.

Figure 36:
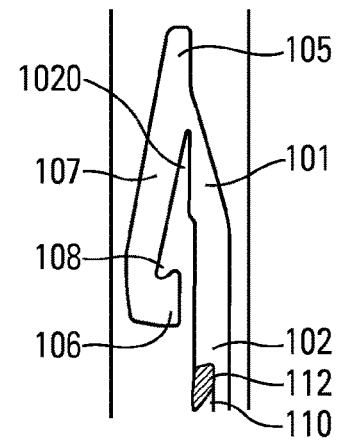
FIGS. 36 to 38 are diagrammatic and fragmentary views showing variant embodiments of the pricking lock.
Figure 37:
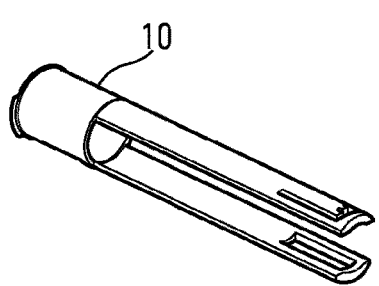
Figure 38:
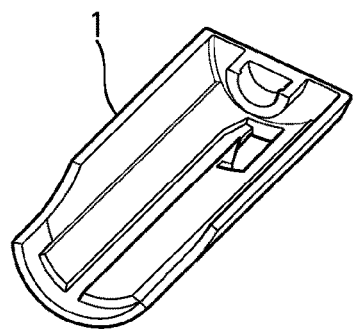

It should be observed that the above-described means could be achieved in inverted manner, i.e. the body 1 (or an element that is secured to said body 1, such as the reservoir support) could include the various grooves and shoulder, and the actuator sleeve 10 could include the flexible tab 110. Naturally, in this configuration, the shapes and orientations of said grooves would be adapted accordingly. FIGS. 36 to 38 are diagrams showing such a variant.

Although the present invention is described above with reference to advantageous embodiments, naturally various modifications can be applied thereto by the person skilled in the art, without going beyond the ambit of the present invention, as defined by the accompanying claims.

The invention claimed is:

1. A manual injection device comprising:
    a lower body that receives a reservoir (S), said reservoir being stationary axially relative to said lower body and containing fluid to be injected, said reservoir (S) including a piston (P) and a needle (A);
    an upper body that is movable axially relative to said lower body during actuation, said upper body including a piston rod (TP) that co-operates with said piston (P) during injection so as to move said piston in the reservoir (S); and
    an actuator sleeve that includes a contact end for coming into contact with a user's body, said actuator sleeve being movable relative to said lower body between a projecting position in which said actuator sleeve projects, at least in part, out from said lower body, and an actuated position in which said actuator sleeve is moved axially into said lower body, said actuator sleeve being in a first projecting position before the manual injection device has been actuated, and in a second projecting position after the manual injection device has been actuated;
    wherein said actuator sleeve co-operates with said lower body, or with an element that is secured to said lower body to define a pricking lock, and said piston rod (TP) co-operates with said reservoir (S), or with an element that is secured to said reservoir (S) to define an injection lock, the force necessary for actuating said pricking lock being less than the force necessary for actuating said injection lock, such that said pricking lock is actuated before said injection lock;
    wherein said piston rod includes a central recess that defines two flexible branches that slope radially away from each other so as to form a radially-outer shoulder on each side of said piston rod; and
    said radially-outer shoulders co-operate with a radial collar of said reservoir.

2. A manual injection device according to claim 1, wherein one of said actuator sleeve or said lower body, or any element that is secured to said lower body, includes a flexible tab that is adapted to deform laterally relative to said actuator sleeve and/or relative to said lower body when said actuator sleeve is moved from its first projecting position to its actuated position, and then from its actuated position while returning to its second projecting position, the other of said actuator sleeve and said body, or any element that is secured to said lower body, including an initial zone that co-operates with said flexible tab in said first projecting position, an intermediate zone that co-operates with said flexible tab in said actuated position, and a final reception zone that co-operates with said flexible tab in said second projecting position, said final reception zone being offset, at least laterally, from said initial zone.

3. A manual injection device according to claim 2, wherein a deformable axial wall is adapted to deform resiliently so as to allow said flexible tab to pass from said initial zone to said intermediate zone, said deformable axial wall, in its non-deformed position, then being adapted to guide said flexible tab from said intermediate zone to said final reception zone.

4. A manual injection device according to claim 2, wherein said final reception zone is connected to said intermediate zone via a final groove, an axial shoulder being provided between said final reception zone and said final groove, said flexible tab being adapted to slide in said final groove when said actuator sleeve returns from its actuated position to its second projecting position, said flexible tab becoming snap-fastened below said axial shoulder when said actuator sleeve reaches its second projecting position after use, thereby locking said actuator sleeve relative to said lower body.

5. A manual injection device according to claim 1, wherein said radially-outer shoulders co-operate with an axial flange that is secured to an element that is fastened to said lower body.

6. The manual injection device according to claim 1, wherein the element that is secured to said lower body is a reservoir support.

7. The manual injection device according to claim 1, wherein the element that is secured to said reservoir is a reservoir support or is said lower body.

8. The manual injection device according to claim 1, wherein, before actuation, said piston rod is connected to a ring that is crimped on a radial collar of said reservoir, said ring including a radially-inner projection that, before actuation, co-operates with a groove of said piston rod.

9. A manual injection device comprising:
a lower body that receives a reservoir, said reservoir being stationary axially relative to said lower body and containing fluid to be injected, said reservoir including a piston and a needle;
an upper body that is movable axially relative to said lower body during actuation, said upper body including a piston rod that co-operates with said piston during injection so as to move said piston in the reservoir; and
an actuator sleeve that includes a contact end for coming into contact with a user's body, said actuator sleeve being movable relative to said lower body between a projecting position in which said actuator sleeve projects, at least in part, out from said lower body, and an actuated position in which said actuator sleeve is moved axially into said lower body, said actuator sleeve being in a first projecting position before the manual injection device has been actuated, and in a second projecting position after the manual injection device has been actuated;
wherein said actuator sleeve co-operates with said lower body, or with an element that is secured to said lower body to define a pricking lock, and said piston rod co-operates with said reservoir, or with an element that is secured to said reservoir to define an injection lock, the force necessary for actuating said pricking lock being less than the force necessary for actuating said injection lock, such that said pricking lock is actuated before said injection lock;
wherein said piston rod includes a central recess that defines two flexible branches that slope radially away from each other so as to form a radially-outer shoulder on each side of said piston rod; and
wherein each radially-outer shoulder defines an indented profile, said indented profiles receiving a radial projection of an axial flange that is secured to an element that is fastened to said lower body.

10. The manual injection device according to claim 9, wherein one of said actuator sleeve or said lower body, or any element that is secured to said lower body, includes a flexible tab that is adapted to deform laterally relative to said actuator sleeve and/or relative to said lower body when said actuator sleeve is moved from its first projecting position to its actuated position, and then from its actuated position while returning to its second projecting position, the other of said actuator sleeve and said body, or any element that is secured to said lower body, including an initial zone that co-operates with said flexible tab in said first projecting position, an intermediate zone that co-operates with said flexible tab in said actuated position, and a final reception zone that co-operates with said flexible tab in said second projecting position, said final reception zone being offset, at least laterally, from said initial zone.

11. A manual injection device comprising:
a lower body that receives a reservoir, said reservoir being stationary axially relative to said lower body and containing fluid to be injected, said reservoir including a piston and a needle;
an upper body that is movable axially relative to said lower body during actuation, said upper body including a piston rod that co-operates with said piston during injection so as to move said piston in the reservoir; and
an actuator sleeve that includes a contact end for coming into contact with a user's body, said actuator sleeve being movable relative to said lower body between a projecting position in which said actuator sleeve projects, at least in part, out from said lower body, and an actuated position in which said actuator sleeve is moved axially into said lower body, said actuator sleeve being in a first projecting position before the manual injection device has been actuated, and in a second projecting position after the manual injection device has been actuated;
wherein said actuator sleeve co-operates with said lower body, or with an element that is secured to said lower body to define a pricking lock, and said piston rod co-operates with said reservoir, or with an element that is secured to said reservoir to define an injection lock, the force necessary for actuating said pricking lock being less than the force necessary for actuating said injection lock, such that said pricking lock is actuated before said injection lock;
wherein, before actuation, said piston rod is connected via breakable bridges to an element that is stationary relative to said reservoir; and
wherein, before actuation, said piston rod (TP) is connected to a disk that is fastened to said lower body.

12. The manual injection device according to claim 11, wherein one of said actuator sleeve or said lower body, or any element that is secured to said lower body, includes a flexible tab that is adapted to deform laterally relative to said actuator sleeve and/or relative to said lower body when said actuator sleeve is moved from its first projecting position to its actuated position, and then from its actuated position while returning to its second projecting position, the other of said actuator sleeve and said body, or any element that is secured to said lower body, including an initial zone that co-operates with said flexible tab in said first projecting position, an intermediate zone that co-operates with said flexible tab in said actuated position, and a final reception zone that co-operates with said flexible tab in said second projecting position, said final reception zone being offset, at least laterally, from said initial zone.

13. A manual injection device comprising:
a lower body that receives a reservoir, said reservoir being stationary axially relative to said lower body and containing fluid to be injected, said reservoir including a piston and a needle;
an upper body that is movable axially relative to said lower body during actuation, said upper body including a piston rod that co-operates with said piston during injection so as to move said piston in the reservoir; and
an actuator sleeve that includes a contact end for coming into contact with a user's body, said actuator sleeve being movable relative to said lower body between a projecting position in which said actuator sleeve projects, at least in part, out from said lower body, and an actuated position in which said actuator sleeve is moved axially into said lower body, said actuator sleeve being in a first projecting position before the manual injection device has been actuated, and in a second projecting position after the manual injection device has been actuated;
wherein said actuator sleeve co-operates with said lower body, or with an element that is secured to said lower body to define a pricking lock, and said piston rod co-operates with said reservoir, or with an element that is secured to said reservoir to define an injection lock, the force necessary for actuating said pricking lock being less than the force necessary for actuating said injection lock, such that said pricking lock is actuated before said injection lock;
wherein, before actuation, said piston rod is connected via breakable bridges to an element that is stationary relative to said reservoir; and
wherein, before actuation, said piston rod (TP) is connected to a ring that is fastened particular crimped, on a radial collar of said reservoir (S).

14. The manual injection device according to claim 13, wherein, before actuation, said piston rod is connected to a ring that is crimped on the radial collar of said reservoir.

15. A manual injection device comprising:
a lower body that receives a reservoir, said reservoir being stationary axially relative to said lower body and containing fluid to be injected, said reservoir including a piston and a needle;
an upper body that is movable axially relative to said lower body during actuation, said upper body including a piston rod that co-operates with said piston during injection so as to move said piston in the reservoir; and
an actuator sleeve that includes a contact end for coming into contact with a user's body, said actuator sleeve being movable relative to said lower body between a projecting position in which said actuator sleeve projects, at least in part, out from said lower body, and an actuated position in which said actuator sleeve is moved axially into said lower body, said actuator sleeve being in a first projecting position before the manual injection device has been actuated, and in a second projecting position after the manual injection device has been actuated;
wherein said actuator sleeve co-operates with said lower body, or with an element that is secured to said lower body to define a pricking lock, and said piston rod co-operates with said reservoir, or with an element that is secured to said reservoir to define an injection lock, the force necessary for actuating said pricking lock being less than the force necessary for actuating said injection lock, such that said pricking lock is actuated before said injection lock;
wherein, before actuation, said piston rod (TP) is connected to a ring that is fastened on a radial collar of said reservoir (S), said ring including a radially-inner projection that, before actuation, co-operates with a groove of said piston rod (TP).

16. The manual injection device according to claim 15, wherein one of said actuator sleeve or said lower body, or any element that is secured to said lower body, includes a flexible tab that is adapted to deform laterally relative to said actuator sleeve and/or relative to said lower body when said actuator sleeve is moved from its first projecting position to its actuated position, and then from its actuated position while returning to its second projecting position, the other of said actuator sleeve and said body, or any element that is secured to said lower body, including an initial zone that co-operates with said flexible tab in said first projecting position, an intermediate zone that co-operates with said flexible tab in said actuated position, and a final reception zone that co-operates with said flexible tab in said second projecting position, said final reception zone being offset, at least laterally, from said initial zone.

* * * * *